United States Patent
Hill et al.

(10) Patent No.: US 8,781,590 B2
(45) Date of Patent: Jul. 15, 2014

(54) METHOD OF PRODUCING A PROXIMAL CONNECTOR END OF AN IMPLANTABLE LEAD

(75) Inventors: Rolf Hill, Jarfalla (SE); Andreas Ornberg, Jarfalla (SE); Eva Micski, Jarfalla (SE); Henrik Djurling, Jarfalla (SE); Mats Nygren, Bromma (SE)

(73) Assignee: St. Jude Medical AB, Jarfalla (SE)

( * ) Notice: Subject to any disclaimer, the term of this patent is extended or adjusted under 35 U.S.C. 154(b) by 76 days.

(21) Appl. No.: 13/557,009

(22) Filed: Jul. 24, 2012

(65) Prior Publication Data

US 2012/0290060 A1  Nov. 15, 2012

Related U.S. Application Data

(62) Division of application No. 12/741,611, filed as application No. PCT/SE2007/001007 on Nov. 14, 2007, now Pat. No. 8,250,749.

(51) Int. Cl.
*A61N 1/375* (2006.01)
*A61N 1/05* (2006.01)
*H01R 43/20* (2006.01)
*H01R 24/58* (2011.01)

(52) U.S. Cl.
CPC *A61N 1/05* (2013.01); *H01R 43/20* (2013.01); *H01R 2201/12* (2013.01); *A61B 2562/227* (2013.01); *A61N 1/3752* (2013.01); *H01R 24/58* (2013.01)
USPC ................ 607/37; 607/36; 600/394

(58) Field of Classification Search
CPC ............ A61N 1/3752; A61N 1/3968
USPC ...................... 607/36, 37; 600/394
See application file for complete search history.

(56) References Cited

U.S. PATENT DOCUMENTS

| 4,463,765 A | 8/1984 | Gold |
| 4,577,643 A | 3/1986 | Beranek |
| 4,922,607 A | 5/1990 | Doan et al. |
| 4,951,687 A | 8/1990 | Ufford et al. |
| 5,007,435 A | 4/1991 | Doan et al. |
| 5,575,814 A | 11/1996 | Giele et al. |

(Continued)

FOREIGN PATENT DOCUMENTS

| EP | 1162022 B1 | 4/2005 |
| WO | 2006020090 A2 | 2/2006 |
| WO | 2006020090 A3 | 4/2006 |

OTHER PUBLICATIONS

Restriction Requirement, mailed Dec. 13, 2011—U.S. Appl. No. 12/741,611.

(Continued)

*Primary Examiner* — Niketa Patel
*Assistant Examiner* — Christopher A Flory

(57) ABSTRACT

A connector for an implantable medical lead that is electrically and mechanically connectable to an implantable medical device, has a connector pin made of a first conducting material. A tubular insulator made of an insulating material concentrically surrounds at least a portion of the pin. A connector ring made of a second conducting material is concentrically positioned around at least a portion of the insulator. The insulator is connected to the connector ring by spark plasma sintering in the case of an active fixation lead, and is connected to the ring and the pin by spark plasma sintering in the case of a passive fixation lead.

10 Claims, 8 Drawing Sheets

(56) References Cited

U.S. PATENT DOCUMENTS

| | | |
|---|---|---|
| 6,384,365 B1 | 5/2002 | Seth et al. |
| 6,515,250 B2 | 2/2003 | Miyasaka et al. |
| 6,842,649 B2 | 1/2005 | Laabs et al. |
| 8,244,373 B1 * | 8/2012 | Bauer et al. .................. 607/116 |
| 8,250,749 B2 * | 8/2012 | Hill et al. ....................... 29/843 |
| 2004/0098074 A1 | 5/2004 | Erickson et al. |
| 2006/0015187 A1 * | 1/2006 | Hunter et al. ................ 623/23.5 |
| 2012/0324728 A1 * | 12/2012 | Hill et al. ....................... 29/877 |

OTHER PUBLICATIONS

Notice of Allowance, mailed Apr. 26, 2012—U.S. Appl. No. 12/741,611.

* cited by examiner

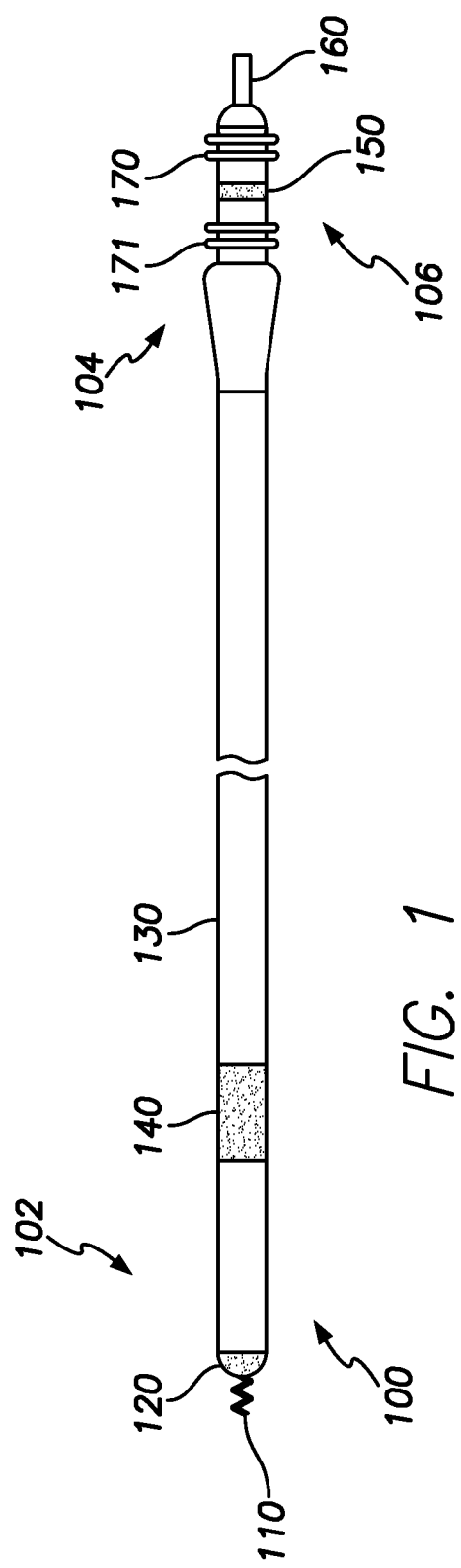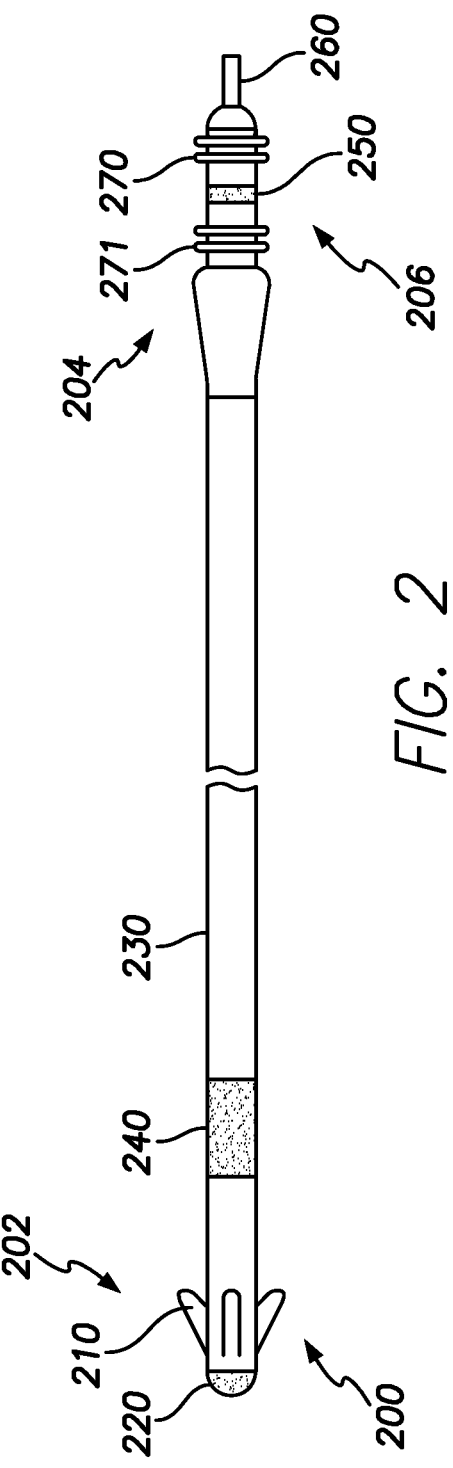

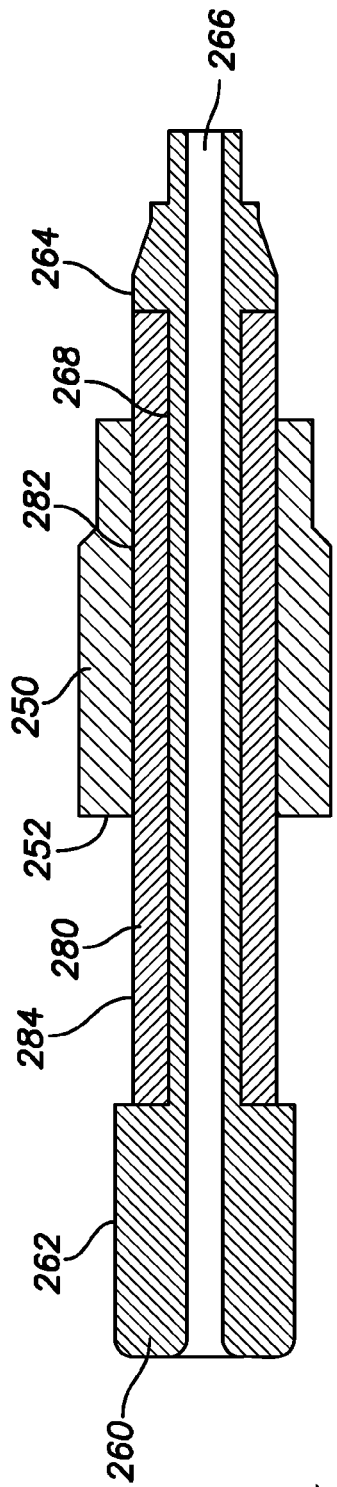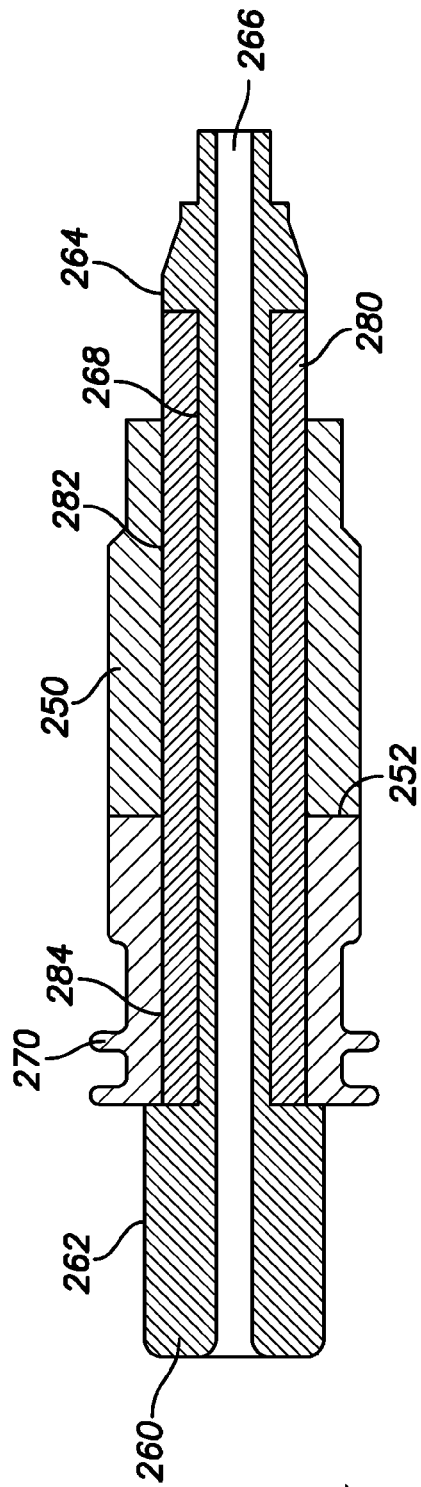

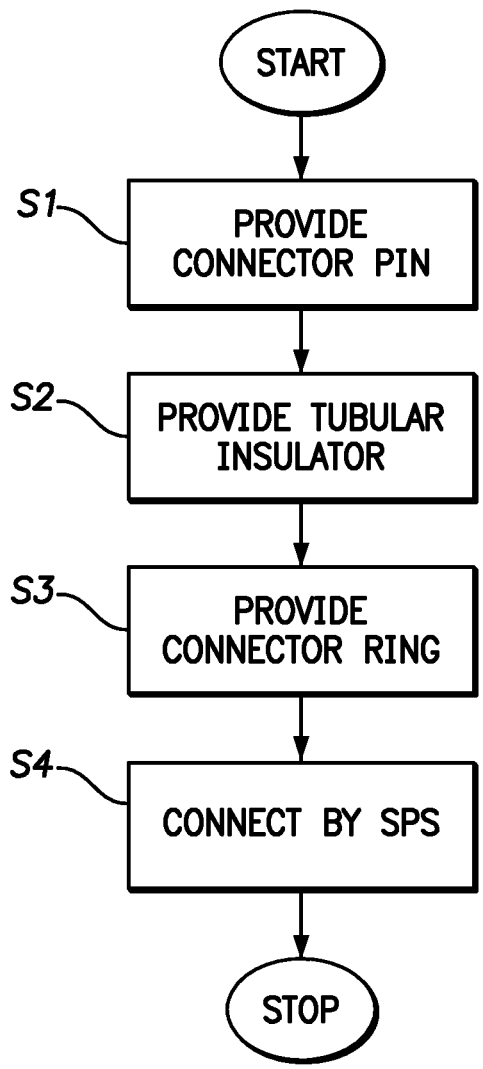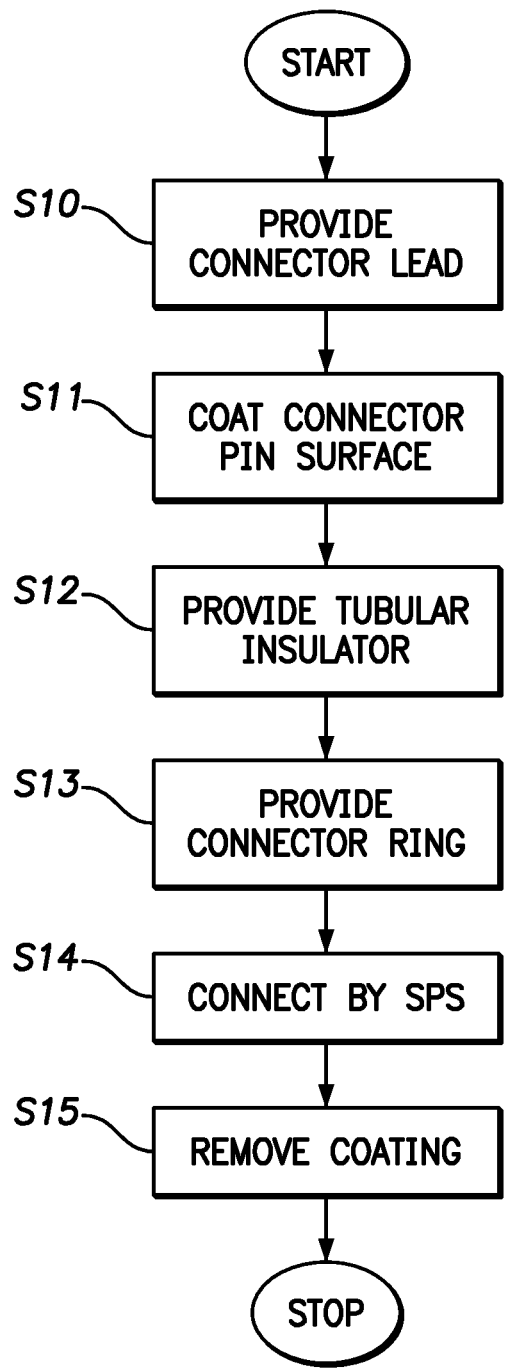
FIG. 9
FIG. 10

METHOD OF PRODUCING A PROXIMAL CONNECTOR END OF AN IMPLANTABLE LEAD

BACKGROUND OF THE INVENTION

1. Field of the Invention

The present invention generally relates to implantable leads, and in particular to proximal end portions for such implantable leads.

2. Description of the Prior Art

Body implantable electrical leads form the electrical connection between an implantable medical device (IMD), such as cardiac pacemaker, cardiac defibrillator or cardioverter, and body tissue, such as the heart, which is to be electrically stimulated. As is well known, the leads connecting the IMD with the tissue may be used for pacing/defibrillation and for sensing electrical signals produced by the tissue.

The implantable leads of today are complex arrangements, generally including multiple different lead elements of different materials and therefore having different characteristics. In particular, connector arrangements or proximal end portions of implantable leads are complex arrangements, generally consisting of a multitude of different lead elements that have to be interconnected to form the final connector. This assembling process is complex and time-consuming having multiple separate sub-assembly steps.

SUMMARY OF THE INVENTION

There is therefore a need for a lead manufacturing process that allows assembling of proximal lead end portions using few including elements and in few assembly steps. The present invention overcomes these and other drawbacks of the prior art arrangements.

It is a general object of the present invention to provide a lead connector comprising mechanically inter-connected connector elements of different materials.

It is another object of the invention to provide a connector arrangement that can be simply handled in the manufacture of lead connectors for implantable medical leads.

Briefly, the present invention involves a connector assembly of an implantable medical lead for providing a mechanical and electrical connection to an implantable medical device.

The connector assembly has a central connector pin made of a first conducting material, such as stainless steel. In a first embodiment adapted for active fixation implantable leads, at least a portion of the outer lateral pin surface is coated with a protective layer. A tubular insulator is concentrically provided around at least a portion of the coated pin. The insulator is made of an electrically insulating material, such as a ceramic. A connector ring made of a second conducting material, such as stainless steel, is concentrically provided around at least a portion of the outer lateral insulator surface. According to the present invention, spark plasma sintering is applied to the assembly for mechanically connecting the connector ring to the tubular insulator. The protective layer prevents the insulator from mechanically bonding to the connector pin. After removal of the protective layer, a spacing is formed between the outer pin surface and the inner insulator surface. As a consequence, the connector pin is rotatable relatively the mechanically inter-connected sub-assembly consisting of the insulator and the ring electrode. However, due to the design of the pin, i.e. having a waist surrounded by proximal and distal lead portions with comparatively larger diameters, the sub-assembly is longitudinally restricted relative the connector pin by these proximal and distal pin portions.

A connector assembly adapted for a passive fixation implantable lead does not have any protective coating on the pin surface. As a consequence, the tubular insulator becomes mechanically connected to both the connector pin and the connector ring.

The invention offers the following advantages:

- Requires fewer lead components for manufacturing a lead connector assembly;
- Allows reliable mechanical inter-connection of connector elements of different materials;
- Simplifies the assembly process;
- Provides a rigid connector design; and
- Same connector elements and similar manufacturing process can be used for both passive and active fixation lead connectors.

Other advantages offered by the present invention will be appreciated upon reading of the below description of the embodiments of the invention.

SHORT DESCRIPTION OF THE DRAWINGS

FIG. 1 is a side view of an implantable active fixation lead according to an embodiment of the present invention.

FIG. 2 is a side view of an implantable passive fixation lead according to an embodiment of the present invention.

FIG. 4 is an axial cross section view of the proximal end portion of an implantable passive fixation medical lead according to an embodiment of the present invention.

FIG. 5 is an axial cross section view of the proximal end portion of an implantable passive fixation medical lead according to FIG. 4 equipped with an insulating seal.

FIG. 9 is a flow diagram illustrating a method of producing a proximal end portion of an implantable passive fixation lead according to an embodiment of the present invention.

FIG. 10 is a flow diagram illustrating a method of producing a proximal end portion of an implantable active fixation lead according to an embodiment of the present invention.

DESCRIPTION OF THE PREFERRED EMBODIMENTS

Figure 3:
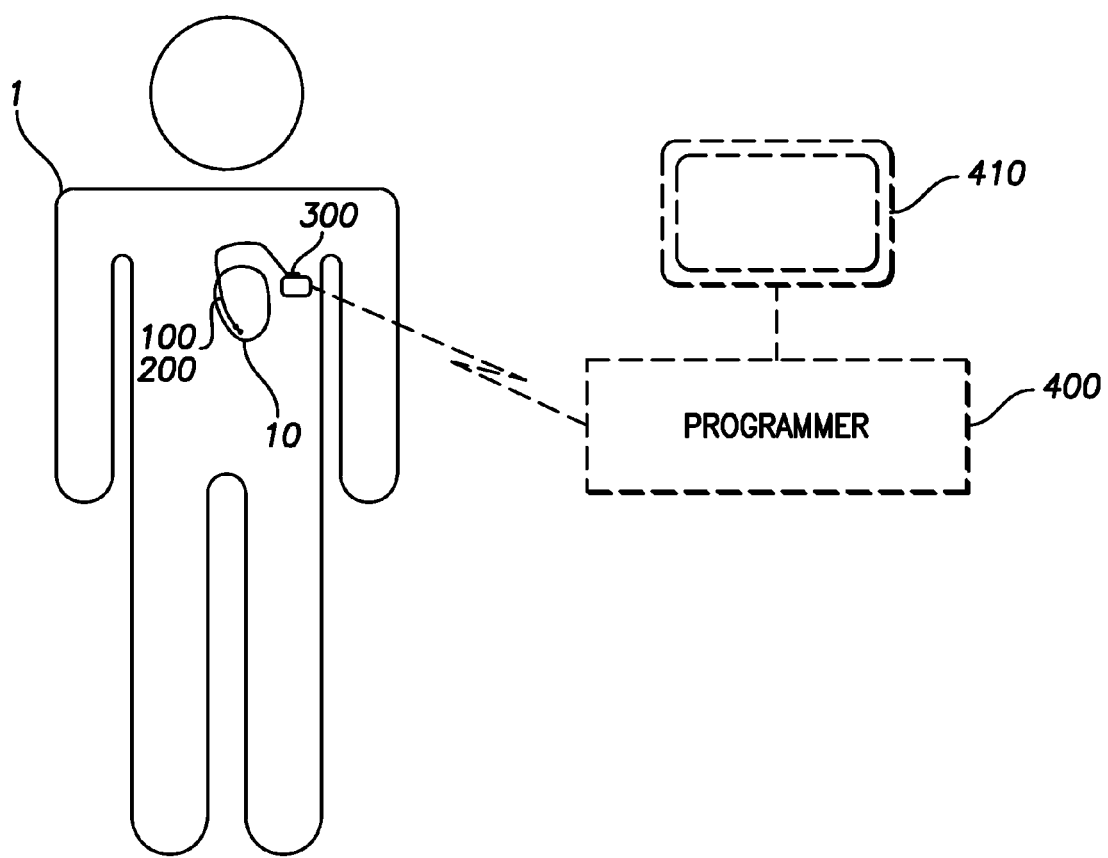
FIG. 3 is a schematic overview of a subject having an implantable medical device connected to an implantable lead according to an embodiment of the present invention.

Throughout the drawings, the same reference characters will be used for corresponding or similar elements.

The present invention relates to implantable medical leads or catheters, and in particular to a connector arrangement in the proximal end of such leads. This connector arrangement of the invention is adapted for connection to different implantable medical devices (IMDs), such as pacemakers, cardioverters, defibrillators and other implantable electrical medical devices.

FIG. 1 is a schematic illustration of an implantable lead 100 according to an embodiment of the present invention. The lead 100 comprises a lead body 130 extending a long a central, longitudinal axis. The lead 100 has a proximal end 106 carrying a connector assembly 104 for electrically connecting the lead body 130 to an IMD. The lead 100 also has a distal end 102 comprising a header with electrodes 120, 140 and fixation elements 110. The lead 100 has non-limitedly been illustrated in the form of a so-called active fixation medical lead 100, implying that the fixation element 110 is in the form of a helical, screw-in fixation element 110 adapted to be extended so as to project from the distal end of the header. The helical screw-in fixation element 110 is preferably active electrically so as to function as an electrode when implanted to stimulate selected tissue, such as cardiac tissue, and/or sense electrical activity of the tissue. Consistent with teachings well known in the art, one or more portions of such a helical electrode 110 may be electrically insulated along its length. The helical electrode 110 not only has a stimulating and/or sensing function but also serves to anchor or stabilize the distal lead portion 102 relative to the tissue.

The distal lead portion 102 also has a ring electrode 140 or indifferent electrode for electrically stimulating adjacent tissue and/or for sensing electrical activity of tissue. An optional tip electrode 120 may be provided at the most distal end 102 of the lead 100 as is well known in the art. The tip electrode 120 may optionally be made of a radiopaque material for facilitating monitoring implantation of the lead 100 into a patient body.

The connector assembly 104 at the proximal lead end 106 is adapted to electrically and mechanically couple the lead body 130 to the IMD. The assembly comprises terminal contacts in the form of a tubular, rotatable pin terminal contact 160, often denoted connector pin 160, and a ring terminal contact 150, generally referred to as connector ring 150. These two contacts 150, 160 are positioned to engage corresponding electrical terminals within a receptacle in the IMD. In order to prevent ingress of body fluid into the IMD receptacle, the connector assembly may be provided with spaced-apart sets of seals 170, 171, well known in the art.

FIG. 2 is an illustration of another embodiment of a lead 200 to which the teachings of the present invention can be applied. This lead 200 is a so called passive fixation lead, where the helical screw-in fixation element has been replaced by, for instance a collar, fines or, as in the figure, tines 210 for anchoring the lead body 230 to a selected tissue.

The passive fixation lead 200 has a distal end 202 with an optional, preferably radiopaque, tip electrode 220 and a ring electrode 240. The proximal lead end 206 has a connector assembly 204 according to the present invention with an electrically conducting connector pin 260 and connector ring 250. These two terminals 250, 260 are adapted for connection to matching electrical terminal in a receptacle of the IMD. The connector 204 preferably also comprises seal rings 270, 271 for preventing body fluids from entering the IMD receptacle.

In clear contrast to the connector pin of the active fixation lead in FIG. 1, the connector pin 260 does not have to be rotatable relative the lead body 230 in this embodiment as no screwing fixation element is present.

FIG. 3 is a schematic overview of a subject 1 equipped with an IMD 300 connected to the subject's heart 10. The IMD 300 is illustrated as a device that monitors and/or provides therapy to the heart 10 of the patient 1, such as a pacemaker, defibrillator or cardioverter. However, the present invention is not limited to cardiac-associated IMDs but may also be practiced with other implantable medical devices, such as drug pumps, neurological stimulators, physical signal recorders, oxygen sensors, or the like, as long as the IMD 300 is equipped with or is connected to at least one medical lead 100, 200 according to the present invention.

The IMD 300 can wirelessly communicate with an external device 400, non-limitedly illustrated as a programmer 400 in the figure. The external device 400 could alternatively be a physician's workstation, a home monitoring device or actually any data processing unit having capability of receiving data collected by the IMD 300 and preferably sending instructions and commands to the IMD 300. The external device 400 is preferably connected to a display screen 410 allowing display of the collected diagnostic parameters and data.

The present invention provides a novel bonding technique used for mechanically connecting connector elements of different material to obtain a robust and reliable mechanical connection. Traditionally, a multitude of different connecting techniques have been used in the art, including snap-fit solutions, adhesions, welds, etc. These known connecting techniques have pros and cons. A general problem is that the assembly generally becomes time-consuming and complex, as an operator has to simultaneously handle multiple separate lead components that are to be inter-connected. Furthermore, the number of connecting techniques in the prior art of implantable lead assembly when connecting conducting metal-based lead elements with non-conducting non-metal elements has been rather limited. Generally, one may be limited to using different adhesions and like, making the assembly processes complex and time-consuming.

The present invention takes a radically different approach by utilizing spark plasma sintering for mechanically inter-connecting different connector elements to achieve a highly robust, reliable and corrosion- and strain-resisting connection. The spark plasma sintering technique has the further advantage in not being limited to be applied to metal and metal-based materials but can also be used for inter-connecting a conducting element, such as made of metal (alloy) material, to a non-conducting element, for instance made of a ceramic material.

FIG. 4 is a cross-sectional view of a proximal connector end 204 of a passive fixation implantable lead according to the present invention. The connector assembly 204 comprises a connector pin 260 made of a first conducting material. This material is selected from the group including metals, such as platinum, titanium, tantalum, iridium and niobium, and different alloys thereof, such as titanium alloys or platinum/iridium (Pt/Ir) alloys, including Pt/Ir 90/10 or Pt/Ir 80/20. Also other metal alloy materials can be used, including nickel-cobalt-chromium-molybdenum alloys, such as MP35N® (trademark of SPS Technologies, Inc.) or 35N LT® (trademark of Fort Wayne Metals Research Products Corp.), or iron-nickel-cobalt alloys, such as Kovar® (trademark of Carpenter Technology Corp.). Further suitable materials include stainless steel, preferably stainless steel of medical grade, such as medical grade 316L stainless steel.

The proximal end portion 262 of the connector pin 260 is adapted for electrical connection to a mating terminal at a receptacle of the IMD. The distal end portion 264 of the pin 260 is adapted for connection to an inner conductor coil that runs through the length of the lead body for connection with one of the electrodes (tip or ring electrode) at the lead header.

The connector pin 260 has a longitudinally running bore 266 through which a stylet or guide wire can be inserted through the bore 266 of the pin 260 and into a longitudinal passageway within the lead body for the purpose of delivering and steering the distal portion of the lead during implantation.

A tubular insulator 280 made of an insulating material is concentrically positioned around a portion 268 of the connector pin 260. The insulator 280 is, in this embodiment of the invention, mechanically connected to the pin 260 by spark plasma sintering. Thus, an inner surface of the insulator 280 is at least partly connected to the lateral surface of a portion 268 of the connector pin 260. The insulator 280 preferably covers an intermediate portion 268 of the pin lateral surface between the proximal end 262 for electrical connection to an IMD terminal and the distal end 264 for mechanical and electrical connection to the inner conductor coil. In a preferred embodiment, the covered pin portion 268 presents a smaller outer diameter as compared to the end portions 262, 264. As a consequence, tubular insulator 280 can be formed and connected to the pin 260 in a waist of the connector pin 260.

The tubular insulator 280 is made of an insulating material that can be spark plasma sintered to the conducting material of the connector pint 260. Preferred such insulating materials include ceramic materials, including alumina oxide ($Al_2O_3$), zirconium dioxide ($ZrO_2$) and potassium sodium niobate (KNN) ceramics ($K_xNa_yNbO_3$). Other possible insulating materials include hydroxylapatite ($Ca_5(PO_4)_3(OH)$), magnesium oxide (MgO) and silicon dioxide ($SiO_2$). Also mixtures of any combination of at least two of the above-mentioned insulating materials can be used according to the invention.

The connector assembly 204 also comprises a connector ring 250 made of a second conducting material concentrically positioned around at least a portion 282 of the tubular insulator 280. The connector ring 250 is adapted for electrical connection to an electrode terminal in the IMD receptacle. A distal end of the connector ring 250 is adapted for mechanical and electrical connection to an outer conductor coil that will run through the length of the lead body and end at the ring electrode or tip electrode in the lead header.

The connector ring 250 is mechanically connected to the tubular insulator 280 by spark plasma sintering to achieve a reliable and robust connection even though the two connector elements are made of different materials. The tubular insulator 280 electrically separates the two conducting elements 250, 260 and therefore effectively functions as an insulator therebetween.

The connector ring 250 preferably only covers a sub-portion 282 of the lateral surface of the insulator 280. As a consequence, a remaining portion 284 is bare and may be covered by a seal 270, which is illustrated in FIG. 5. The seal 270, which may be of silicone rubber, polyurethane, a Elast-Eon® polymer (trademark of Aor Tech International, a polymer of silicone with polyurethane), such as Elast-Eon® 2A, 2D, 3A, 3LH or HF, or like, is preferably attached to the surface of remaining insulator portion 284 and the proximal end surface 252 of the connector ring 250 utilizing a medical glue or adhesive.

The second conducting material of the connector ring 250 may be selected from the group including metals, such as platinum, titanium, tantalum, iridium and niobium, and different alloys thereof, such as titanium alloys or platinum/iridium (Pt/Ir) alloys, including Pt/Ir 90/10 or Pt/Ir 80/20. Also other metal alloy materials can be used including a nickel-cobalt-chromium-molybdenum alloy, such as MP35N® (trademark of SPS Technologies, Inc.) or 35N LT® (trademark of Fort Wayne Metals Research Products Corp.), or an iron=nickel-cobalt alloy, such as Kovar® (trademark of Carpenter Technology Corp.). Further suitable materials include stainless steel, preferably stainless steel of medical grade, such as medical grade 316L stainless steel. The ring 250 can advantageously be made of the same conducting material as the connector pin 260.

In this embodiment, the connector ring 250, tubular insulator 280 and connector pin 260 are mechanically interconnected by spark plasma sintering to form a connector assembly 204. Thus, spark plasma sintering is used for connecting an outer surface of a portion 268 of the connector pin 260 to an inner surface of the insulator 280 and for connecting an outer surface of a portion 282 of the insulator 280 to an inner surface of the connector ring 250. The connector assembly 204 can then be handled as a single unit during the remaining lead assembling process, which thereby significantly reduces the complexity and time of the lead manufacturing.

In the above-described connector embodiment all the connector elements are mechanically connected and thereby cannot be separately moved or rotated relative each other. Such connectors are useful for passive fixation leads in which there is no need for being able to extend or retract a helical screw-in fixation element at the distal lead end by manipulating the proximal lead end.

Figure 6:
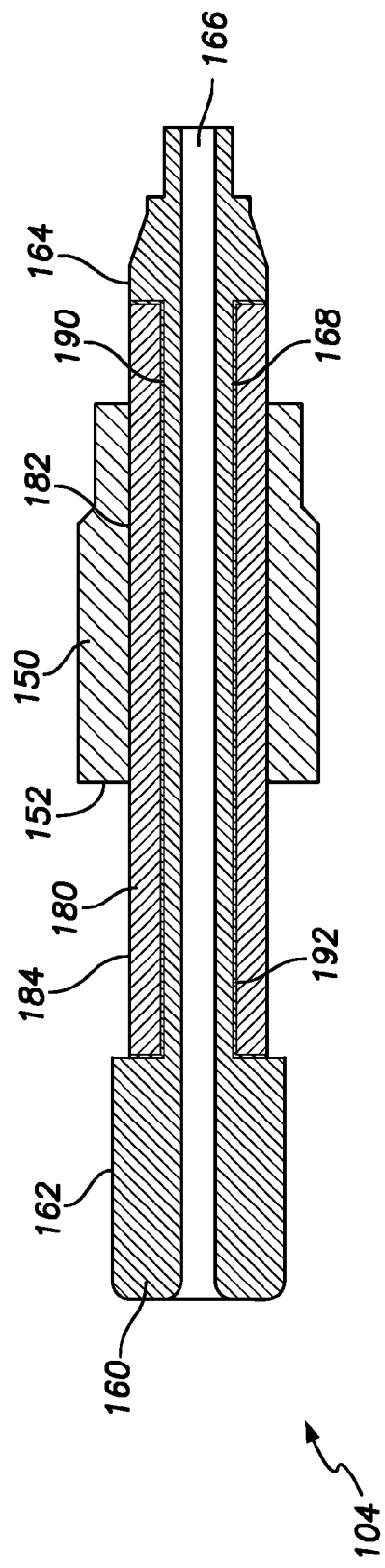
FIG. 6 is an axial cross section view of the proximal end portion of an implantable active fixation medical lead according to an embodiment of the present invention.
Figure 7:
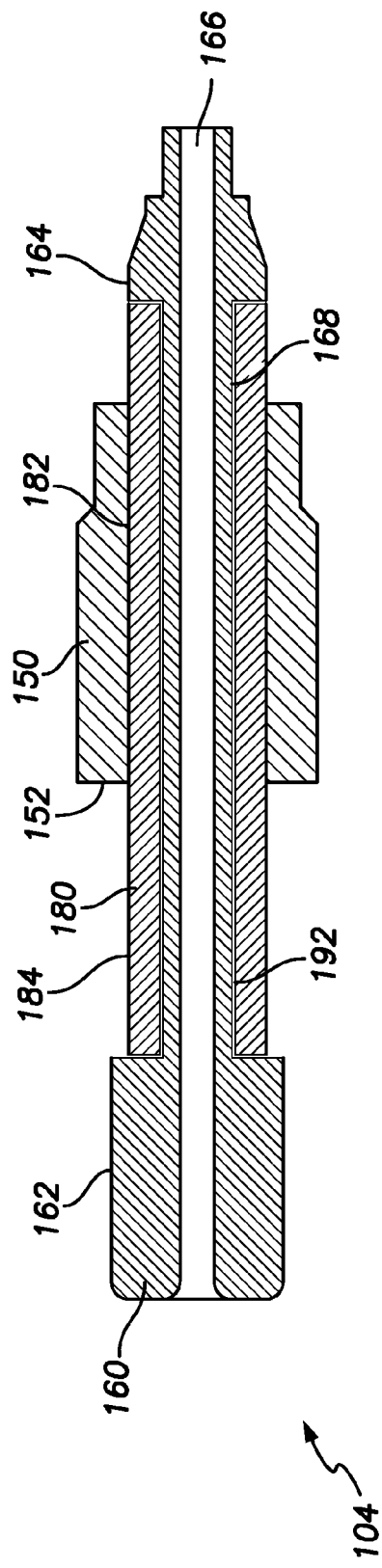
FIG. 7 is an axial cross section view of the proximal end portion of an implantable active fixation medical lead according to FIG. 6, in which the protective coating has been removed.
Figure 8:
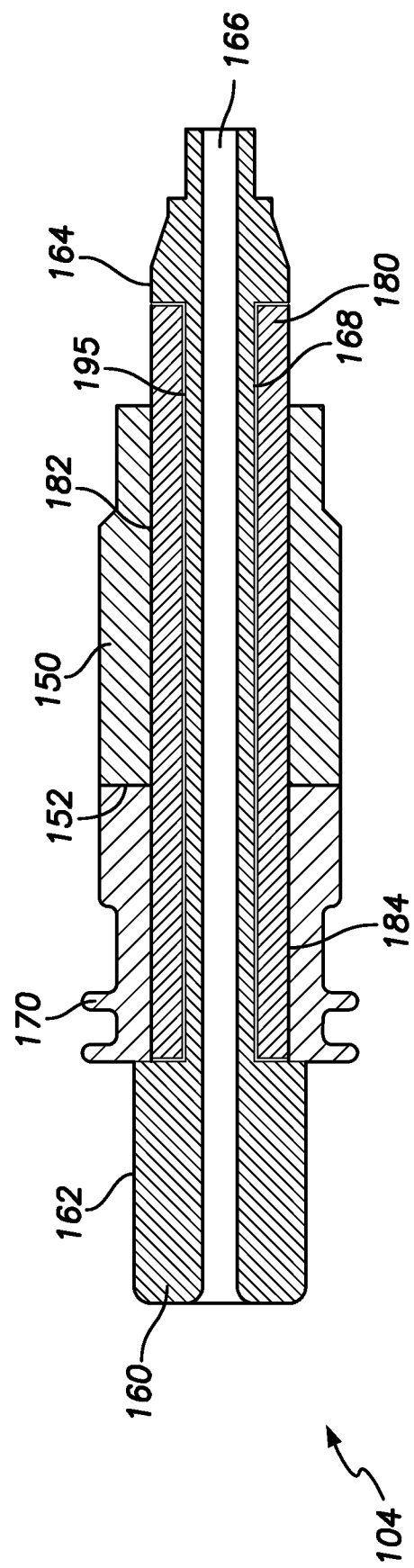
FIG. 8 is an axial cross section view of the proximal end portion of an implantable active fixation medical lead according to FIG. 7 equipped with an insulating seal.

A connector assembly 104 useful in active fixation leads is illustrated in FIGS. 6 to 8. The connector 104 includes the connector pin 160 made of the first conducting material, preferably having a central bore or channel 166. A proximal pin end 162 is adapted for connection to a terminal at the IMD receptacle with a distal pin end 164 is to be mechanically and electrically connected to the inner conductor coil of the lead, electrically inter-connecting the connector pin 160 to an electrode, typically the helix electrode, at the lead header.

A tubular insulator 180 made of an insulating material is concentrically provided around a portion 168 of the connector pin 160. However, in clear contrast to the connector assembly illustrated in FIGS. 4 and 5, the insulator 180 does not become mechanically connected to the connector pin 160 during the spark plasma sintering process in this embodiment. The reason for this is that a protective layer 190 (see FIG. 6) is coated on the lateral surface of at least a portion 168 of the connector pin 160 before initiating the spark plasma process. The coating 190 is also applied to the end surfaces of the proximal pin 162 and the distal pin end 164 facing each other. Alternatively, the whole outside surface of the connector pin 160 is coated with the protective layer 190. This protective layer 190 is then removed after the SPS-process to thereby create a gap 195 (see FIGS. 7 and 8) between the tubular insulator 180 and the pin 160. The usage of such a protective layer 190 means that the inner diameter of the insulator 180 is slightly larger than the outer diameter of the insulated waist portion 168 of the connector pin 160. As a consequence, the pin 160 is rotatable relative the insulator 180 thereby forming a bearing.

The proximal 162 and distal 164 pin portions having larger outer diameters than the intermediate insulated pin portion 168 prevents any significant longitudinal movement of the tubular insulator 180 relative the connector pin 160. The insulator 180 is thereby longitudinally limited in the pin waist. The pin end portions 162, 164 can therefore be regarded as radially protruding shoulders or flanges, which will limit any longitudinal movement of the insulator 180.

The connector ring 150 made of the second conducting material is then concentrically positioned around at least a portion 182 of the tubular insulator 180. The ring 150 is furthermore mechanically connected to the insulator 160 through spark plasma sintering. Thus, an inner surface of the connector ring 150 is mechanically connected to the lateral surface of at least a portion 182 of the insulator 180. As the connector ring 150 becomes attached and anchored to the insulator 180, the connector pin 180 is also rotatable relative the connector ring 150.

A remaining non-covered surface 184 of the tubular insulator 180 is then preferably covered by one or more seals 170 as is illustrated in FIG. 8.

FIG. 9 is a flow diagram illustrating a method of producing a proximal connector assembly of an implantable passive fixation lead according to the present invention. The method involves providing an at least partly fabricated connector pin made of a first conducting material in step S1.

According to the present invention "at least partly fabricated" means a sub-assembly that is either a completely fabricated connector element or at least a partly fabricated raw or start material that can be formed into a fabricated element. As a consequence, at least partly fabricated encompasses providing powder, grain, granule or granulate particles of the relevant material compacted to a shape from which the final shape of the element can be fabricated and formed to a continuous body by spark plasma sintering. At least partly fabricated also encompasses a finally fabricated element that is to be connected, such as by spark plasma sintering, to another element of the connector assembly. The expression also covers element bodies between these two extremes such as an continuous element body of the conducting (in the case of connector pin and connector ring) or non-conducting (in the case of tubular insulator) material that is connected, such as by spark plasma sintering, to another element of the connector assembly but having a shape different from the final shape of the element. In such a case, the element body can be further processed, such as turned, ground, etched, subjected to electrical discharge machining (EDM), milled, sawed, drawn, tumbled, swaged, forged, welded, following the connection to form the desired final shape and/or surface treatment.

Step S1 can therefore involve, for instance, providing powder particles of the first conducting material and forming, in a sintering die, the particles to a desired shape. Alternatively, a fabricated connector pin body of the first material, such as illustrated in FIG. 4 or 5, is provided in step S1. Furthermore, the step S1 can involve provided a continuous body, such as a cylinder or tubular body, of the first conducting material, where the body has a shape different from the final shape of the connector pin.

A next step S2 involves concentrically providing an at least partly fabricated tubular insulator made of a non-conducting material around at least a portion of the connector pin. This step S2 can, in consistency with step S1, involve providing powder particles of the non-conducting material and compacting them to a desired shape. Alternatively, a fabricated tubular insulator having a shape as illustrated in FIG. 4 or 5, but having a longitudinal opening allowing the connector pin to be inserted into the lumen of tubular insulator is provided in step S2 or alternatively a continuous but not finally processed tubular insulator body.

Step S3 concentrically provides an at least partly fabricated connector ring made of a second conducting material around at least a portion of the tubular insulator. The connector ring can be provided in the form of particles of the second material compacted around the body or the compacted powder of the tubular insulator. Alternatively, the connector ring can be a body having final shape or a partly fabricated continuous body in which the tubular insulator and the connector pin are threaded.

A next step S4 involves mechanically connecting the tubular insulator to the connector pin and to the connector ring by spark plasma sintering. Furthermore, in the case any of the providing steps S1 to S3 involved providing material particles, the spark plasma sintering operation performed in step S4 also includes forming a continuous body of the material in addition to inter-connecting the connector assembly elements.

"Spark plasma sintering" or "SPS" is a sintering technique that applies, in addition to pressure, DC current/voltage pulses directly through a die containing a sample to be formed or samples to be inter-connected. The DC current pulses not only pass through the die but also through the actual sample(s) in the case of conductive samples. As a consequence, heat is generated internally through spark discharge between the particles occurring in the initial stage of the current-voltage pulse. The generation of spark impact pressure, Joule heat and the action of the electric field will result in efficient heating, plastic deformation promotion, high-speed diffusion and material transfer that give an opportunity to conduct low-temperature, short-time sintering of hard-to-sinter materials and bonding of dissimilar materials.

Spark plasma is formed initially of the sintering process and necks between the particles are created. After the initial process, surface, grain-body and volume-diffusion-processes and plastic flow contribute to densification while avoiding coarsening. SPS also facilitates a very high heating or cooling rate (several hundred ° K/minute), hence the sintering process is very fast. SPS is also sometimes denoted field assisted sintering technique (FAST) or pulsed electric current sintering (PECS) in the art.

Thus, the expression "spark plasma sintering" as used herein relates to a technique for forming bonds between conducting (metal (alloy)) and non-conducting (ceramic) material bodies through the application of pressure and DC current/voltage pulses through the die and the at least partly fabricated connector assembly elements of the invention.

Figure 11:
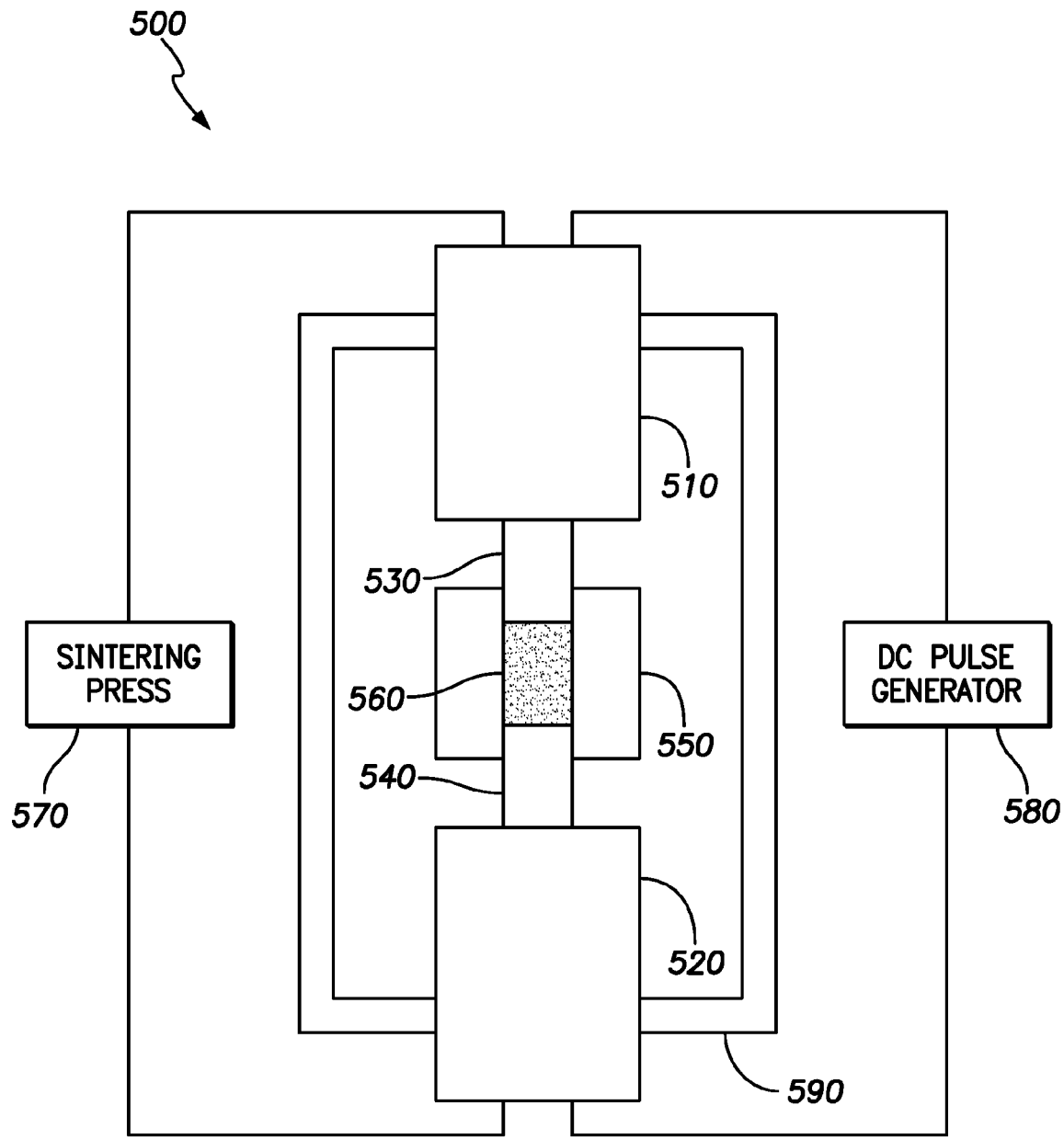
FIG. 11 is a schematic block diagram of a spark plasma sintering apparatus that can be used according to the present invention.

FIG. 11 is a schematic a SPS device 500 that can be used according to the present invention. The device 500 has an upper punch electrode 510 connected to an upper punch 530. A corresponding lower punch electrode 520 is connected to a lower punch 540. The connector assembly elements 560 of the invention to be mechanically connected by SPS according to the present invention are provided in a sintering (graphite) die 550 between the two punches 530, 540. The sample 560 is enclosed together with the punches 530, 540 and the die 550 into a vacuum chamber 590. A DC pulse generator 580 is connected to the upper 510 and lower 530 punch electrode to thereby apply DC current/voltage pulses over the die 550 and through the electrode elements 560. A sintering press 570 is arranged for controlling an exerted pressure applied by the punches 530, 540 to the connector elements 560.

FIG. 10 is a corresponding flow diagram illustrating a method of producing a proximal connector assembly of an implantable active fixation lead according to the present invention. The method starts in step S10, where an at least partly fabricated connector pin made of a first conducting material. This step S10 corresponds to step S1 of FIG. 9 and is not further described. A next step S11 coats or covers at least a portion of an outer surface (lateral surface) of the connector pin with a protective layer. This protective layer is provided to prevent the formation of a mechanical bonding between the connector lead and the tubular insulator. The coating can be applied to only those portions of the connector pin that otherwise would come into contact with insulator material in the SPS process. Alternatively, the whole connector pin surface or at least a major portion thereof can be provided with a protective coating or layer.

There is a vast amount of materials that can be used as protective layer for preventing formation of the mechanical bonding. A first example is salt materials, such as sodium chloride (NaCl) or potassium chloride (KCl). In such a case, a thin coating of the salt can be applied to at least a portion of the outer surface of the connector pin. The application can be in the form of immersing the connector pin in a (high concentration) saline solution and then evaporating away the solvent. Another possible non-salt, protecting material is graphite.

The main characteristic of this protecting material is that it should prevent the insulator from becoming mechanically attached to the connector pin during the SPS and that the shape of the protective layer should be preserved during the SPS process. Furthermore, the protecting material must be removable after the SPS process, without damaging the connector element materials. Any materials that fulfill these requirements can be used according to the invention.

An at least partly fabricated tubular insulator made of a non-conducting material is concentrically provided around at least a portion of the coated portion of the connector pin in step S12. The discussion in connection with step S2 of FIG. 9 applies mutatis mutandis to step S12. Step S13 involves concentrically providing an at least partly fabricated connector ring made of a second conducting material around at least a portion of the tubular insulator. This step S13 corresponds to step S3 of FIG. 9.

The tubular insulator is then mechanically connected to the connector ring by spark plasma sintering in step S14. In addition, if any of the connector elements were provided in the form of material particles, the spark plasma sintering also forms continuous material bodies having a defined (final or processable) shape. In clear contrast to the spark plasma sintering step S4 of FIG. 9, the tubular insulator and the connector pin do not become attached to each other in this step S14 due to the presence of the protective coating. The coating is removed in step S15 from the outer surface of the connector pin to form a spacing between the inner insulator surface and the outer pin surface.

The coating can be removed through different operations, depending on the particular coating material. If the coating consists of a salt layer, the connector assembly can be immersed into a solvent, in which the salt dissolves. Any remaining salt particles can be rinsed of with further solvent, such as water. For non-salt materials, non-aqueous solvents may be required including organic solvents, such as chloroform, alcohols, etc.

Another possible operation can to oxidize away the protective layer together with (mild) heating. For example, a graphite layer can be removed through oxidization at about 400-500° C.

In either case, the coating particle will escape through the (thin) spacings between the short ends of the tubular insulator and the proximal and distal pin portions, respectively.

In an implementation of the invention, the connector pin is provided in the form of a continuous body of the first conducting material, where the body can have the final shape of the connector pin or a more crude shape from which the final shape can be obtained by further processing. The connector pin material can be made of any of the previously mentioned material examples, such as stainless steel of medical grade.

The tubular insulator is preferably provided in the form of non-conducting material particles that are deposited and compacted around a portion of the connector pin. The particles can, for instance, be in the form of spark plasma sinterable ceramic grain/powder/granule/granulate particles, such as $Al_2O_3$ particles.

The connector ring can then be in the form of a partly fabricated or finally fabricated body of the second conducting material or in the form of conducting material particles that are deposited and compacted around a portion of the tubular insulator. The body or particles are preferably made of the same material as the connector pin, such as stainless steel of medical grade.

In another implementation, also the connector pin is provided in the form of conducting material particles that are deposited and compacted in the sintering die in the form of cylinder, preferably hollow cylinder, or more closely to the final pin shape.

A further implementation uses the three connector elements in the form of continuous bodies of the respective materials.

Figure 12A:
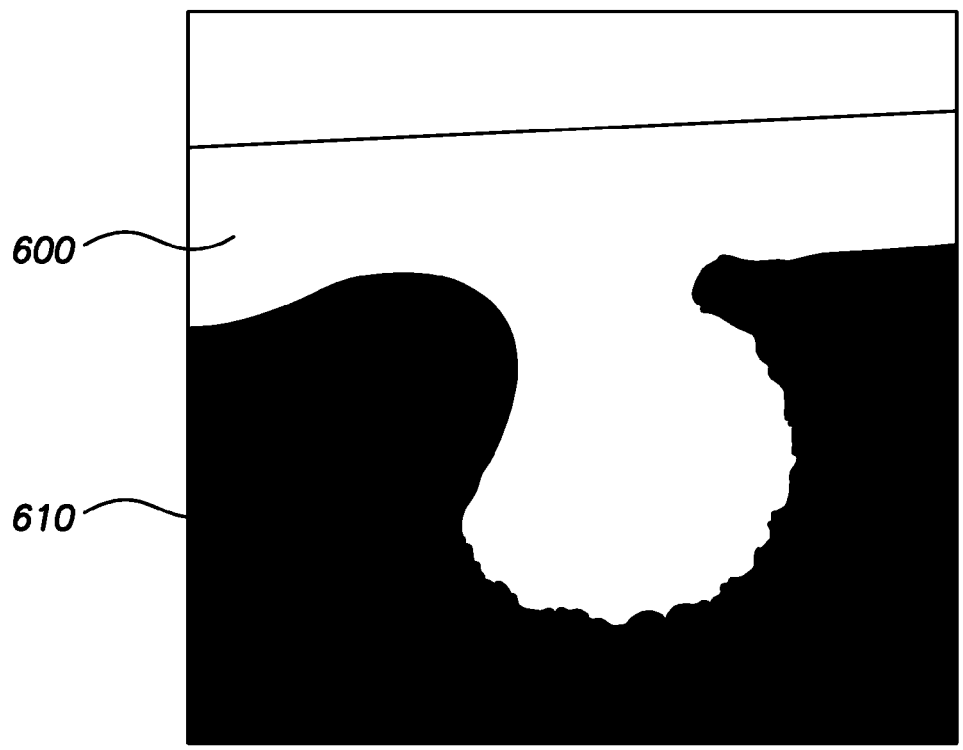
FIGS. 12A and 12B are scanning electron microscope images of a Pt—$Al_2O_3$ connection at 500× magnification (FIG. 12A) and 4000× magnification (FIG. 12B).
Figure 12B:
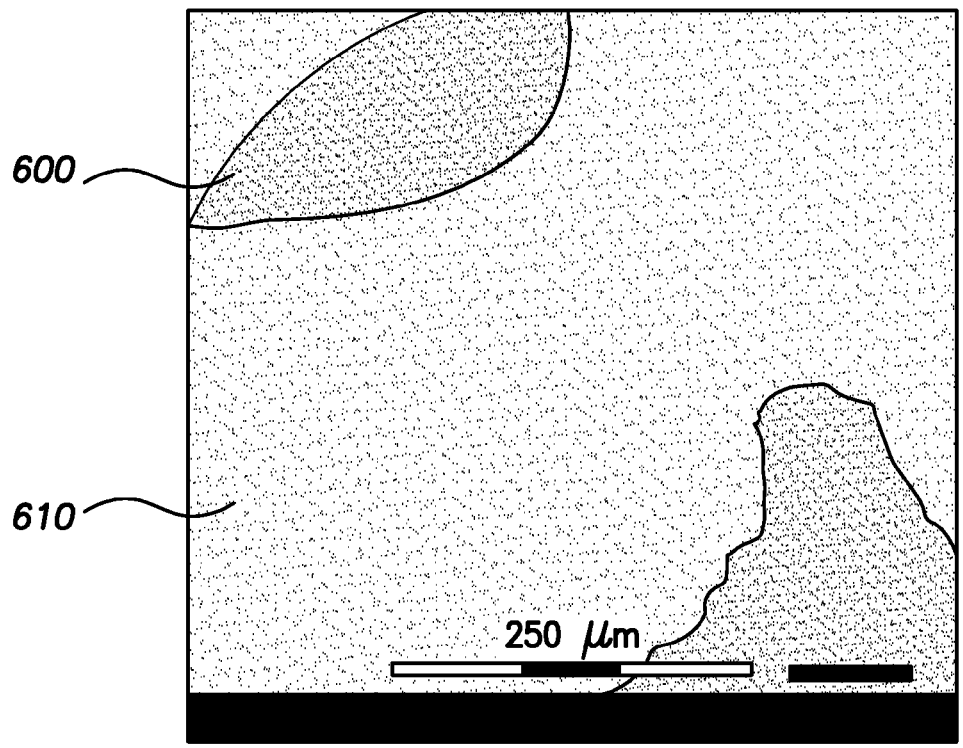

A test body made of a suitable conducting material of the connector pin and/or connector ring, i.e. platinum, and a preferred non-conducting material of the tubular insulator, i.e. $Al_2O_3$, have been spark plasma sintered at a temperature of 1175° C. for 5 minute. The test bodies had a diameter of 10 mm and a height of 3 mm and were sintered from $Al_2O_3$ and platinum powder. FIGS. 12A and 12B are scanning electron microscope images of the joint between the platinum material 610 and the $Al_2O_3$ material 600 at 500× magnification (FIG. 12A) and 4000× magnification (FIG. 12B). As can be seen from the drawings, spark plasma sintering can be used for providing a seamless connection between the two different materials 600, 610 without the formation of any cracks or voids in the joint.

The SPS procedure of the present invention results in a diffusion-based joint between the materials. In a small transition zone around the joint, particles of the materials become inter-mixed to form the diffusion-based, seamless joint.

As is well known in the art, the temperature of the SPS process is dependent on, among others, the particular materials to be sintered and the thickness of the materials or the size of the material particles. Briefly, the sintering temperature should be below the lowest melting point of the materials to the sintered. Furthermore, the smaller the diameter of the material particles, generally the lower sintering temperature can be used. Care must also be taken for materials that are subject to phase transitions so that not an unaccepted, from mechanical and/or electrical properties point of view, is formed in the SPS process. The pressure that is applied during the SPS process is also material dependent and depends on the size of the sintered materials. Generally, the pressure per surface area is rather constant for a given material.

Examples of suitable sintering temperature for some of the materials useful according to the invention include ~1100° C. for $Al_2O_3$, 1000-1100° C. for $ZrO_2$, 700-500° C. for $SiO_2$ and hydroxylapatite, <1100° C. for steel.

The optimal SPS sintering parameters can be determined by the person skilled in the art through routine tests and table look-ups regarding the particular material combinations. The above described parameter settings can be used as starting points in such an optimization process.

It will be understood by a person skilled in the art that various modifications and changes may be made to the present invention without departure from the scope thereof, which is defined by the appended claims.

What is claimed is:

1. A proximal connector end of an implantable lead comprising:
   a connector pin made of a first conducting material;
   a tubular insulator made of an electrically insulating material concentrically positioned around at least a portion of the connector pin;
   a protective layer coating a surface of the connector pin such that the protective layer is disposed between the connector pin and the tubular insulator; and a connector ring made of a second conducting material concentrically positioned around at least a portion of the tubular insulator;

wherein the connector pin, tubular insulator, and connector ring are at least partly connected by spark plasma sintering, wherein the protective layer prevents formation of a mechanical bonding between the connector pin and the tubular insulator, and wherein the protective layer is removed after the spark plasma sintering to create a gap between the tubular insulator and the connector pin to allow rotation of the connector pin relative to the tubular insulator.

2. The proximal connector end according to claim 1, wherein the tubular insulator and the connector ring are collectively rotatable relative to the connector pin.

3. The proximal connector end according to claim 2, wherein the at least a portion of the connector pin constitutes a pin waist flanked by a proximal pin portion and a distal pin portion restricting longitudinal movement of the tubular insulator and the connector ring relative to the connector pin.

4. The proximal connector end according to claim 1, wherein the tubular insulator is connected to the connector pin at least partly by spark plasma sintering.

5. The proximal connector end according to claim 1, wherein the first conducing material is stainless steel.

6. The proximal connector end according to claim 1, wherein the second conducing material is stainless steel.

7. The proximal connector end according to claim 1, wherein the insulating material is a ceramic material.

8. The proximal connector end according to claim 1, wherein the protective layer is a salt material.

9. The proximal connector end according to claim 8, wherein the salt material is sodium chloride (NaCl).

10. The proximal connector end according to claim 8, wherein the salt material is potassium chloride (KCl).

* * * * *